United States Patent
Jiao et al.

(10) Patent No.: US 10,052,019 B1
(45) Date of Patent: Aug. 21, 2018

(54) QUANTITATIVE RETINAL AUTOFLUORESCENCE MAPPING WITH MULTIMODAL IMAGING TECHNOLOGY

(71) Applicants: Shuliang Jiao, Miami, FL (US); Rong Wen, Coral Gables, FL (US); Byron L. Lam, Miami, FL (US)

(72) Inventors: Shuliang Jiao, Miami, FL (US); Rong Wen, Coral Gables, FL (US); Byron L. Lam, Miami, FL (US)

(73) Assignees: The Florida International University Board of Trustees, Miami, FL (US); University of Miami, Miami, FL (US)

( * ) Notice: Subject to any disclaimer, the term of this patent is extended or adjusted under 35 U.S.C. 154(b) by 0 days.

(21) Appl. No.: 15/634,515

(22) Filed: Jun. 27, 2017

(51) Int. Cl.
| | |
|---|---|
| *A61B 3/10* | (2006.01) |
| *A61B 3/12* | (2006.01) |
| *A61B 5/00* | (2006.01) |
| *A61B 3/14* | (2006.01) |
| *A61B 3/00* | (2006.01) |

(52) U.S. Cl.
CPC .......... *A61B 3/1241* (2013.01); *A61B 3/0025* (2013.01); *A61B 3/0041* (2013.01); *A61B 3/102* (2013.01); *A61B 3/14* (2013.01); *A61B 5/0071* (2013.01)

(58) Field of Classification Search
CPC ........... A61B 3/12; A61B 3/14; A61B 3/0025; A61B 3/0008; A61B 3/102; A61B 3/00; A61B 5/7275; A61B 7/0059; A61B 7/0066; A61B 7/0073; G01B 9/02091; G01B 9/02044; G01B 11/22
USPC ...................................................... 351/205
See application file for complete search history.

(56) References Cited

U.S. PATENT DOCUMENTS

| | | | |
|---|---|---|---|
| 2007/0115481 A1* | 5/2007 | Toth ..................... | A61B 3/0025 356/511 |
| 2017/0035291 A1* | 2/2017 | Jiao ........................ | A61B 3/102 |
| 2017/0196459 A1* | 7/2017 | Lam ..................... | A61B 5/0066 |

FOREIGN PATENT DOCUMENTS

WO    WO2015117241 A2 *  2/2015

OTHER PUBLICATIONS

Huang et al., "Optical coherence tomography," Science, Nov. 1991, pp. 1178-1181, vol. 254.
Wojtkowski et al., "Ultrahigh-resolution, high-speed, fourier domain optical coherence tomography and methods for dispersion compensation," Optics Express, May 2004, pp. 2404-2422, vol. 12, No. 11.
Delori et al., "In vivo fluorescence of the ocular fundus exhibits retinal pigment epithelium lipofuscin characteristics," Investigative Ophthalmology and Visual Science, Mar. 1995, pp. 718-729, vol. 36, No. 3.

(Continued)

*Primary Examiner* — Mahidere Sahle
(74) *Attorney, Agent, or Firm* — Saliwanchik, Lloyd & Eisenschenk (57) ABSTRACT

Imaging systems and methods of using the same are provided for monitoring the quantity of fluorescent pigment, for example lipofuscin, in the retinal pigment epithelium (RPE) layer of a retina in vivo. Various imaging modalities can be integrated into a single system and excited by a single broadband light source for the monitoring of the fluorescent pigment. The influence of varying optical properties found in the optical path of the pigment's auto-fluorescence between the RPE and an image receiver can be corrected.

20 Claims, 4 Drawing Sheets

(56) References Cited

OTHER PUBLICATIONS

Boulton et al., "The formation of autofluorescent granules in cultured human RPE," Investigative Ophthalmology and Visual Science, Jan. 1989, pp. 82-89, vol. 30, No. 1.

Johnson, "Age-related macular degeneration and antioxidant vitamins: recent findings," Current Opinion in Clinical Nutrition and Metabolic Care, Jan. 2010, pp. 28-33, vol. 13, Author copy.

Zhang et al., "Dual-band spectral-domain optical coherence tomography for in vivo imaging the spectral contrasts of the retinal nerve fiber layer," Optics Express, Sep. 2011, pp. 19653-19659, vol. 19, No. 20.

Dai et al., "Simultaneous optical coherence tomography and autofluorescence microscopy with a single light source," Journal of Biomedical Optics, Aug. 2012, pp. 080502-1-080502-3, vol. 17, No. 8.

Jiang et al., "Simultaneous optical coherence tomography and lipofuscin autofluorescence imaging of the retina with a single broadband light source at 480nm," Biomedical Optics Express, Nov. 2014, pp. 4242-4248, vol. 5, No. 12.

Yi et al., "Visible-light optical coherence tomography for retinal oximetry," Optics Letters, Jun. 2013, pp. 1796-1798, vol. 38, No. 11, Author Manuscript.

Delori et al., "Quantitative measurements of autofluorescence with the scanning laser ophthalmoscope," Investigative Ophthalmology and Visual Science, Dec. 2011, pp. 9379-9390, vol. 52, No. 13.

Dai et al., "Absolute retinal blood flow measurement with a dual-beam doppler optical coherence tomography," Investigative Ophthalmology and Visual Science, Dec. 2013, pp. 7998-8003, vol. 54, No. 13.

Van De Kraats et al., "The pathways of light measured in fundus reflectometry," Vision Research, Aug. 1996, pp. 2229-2247, vol. 36, No. 15.

Morgan et al., "Scanning laser ophthalmoscope measurement of local fundus reflectance and autofluorescence changes arising from rhodopsin bleaching and regeneration," Investigative Ophthalmology and Visual Science, Mar. 2013, pp. 2048-2059, vol. 54, No. 3.

Jiao et al., "Simultaneous acquisition of sectional and fundus ophthalmic images with spectral-domain optical coherence tomography," Optics Express, Jan. 2005, pp. 444-452, vol. 13, No. 2.

Delori et al., "In vivo measurement of lipofuscin in Stargardt's disease—fundus flavimaculatus," Investigative Ophthalmology and Visual Science, Oct. 1995, pp. 2327-2331, vol. 36, No. 11.

Sparrow et al., "A2E, a byproduct of the visual cycle," Vision Research, Dec. 2003, pp. 2983-2990, vol. 43.

Sparrow et al., "The bisretinoids of retinal pigment epithelium," Progress in Retinal and Eye Research, Mar. 2012, pp. 121-135, vol. 31, No. 2, Author Manuscript.

Strauss, "The retinal pigment epithelium in visual function," Physiological Reviews, Jul. 2005, pp. 845-881, vol. 85.

Kiser et al., "Chemistry of the retinoid (visual) cycle," Chemical Reviews, Jul. 2013, pp. 194-232, vol. 114.

Kevany et al., "Phagocytosis of retinal rod and cone photoreceptors," Physiology, Feb. 2010, pp. 8-15, vol. 25.

Zhang et al., "Simultaneous in vivo imaging of melanin and lipofuscin in the retina with photoacoustic ophthalmoscopy and autofluorescence imaging," Journal of Biomedical Optics, Aug. 2011, pp. 080504-1-080504-3, vol. 16, No. 8.

Zhang et al., "Simultaneous dual molecular contrasts provided by the absorbed photons in photoacoustic microscopy," Optics Letters, Dec. 2010, pp. 4018-4020, vol. 35, No. 23, Author Manuscript.

Zhang et al., "Optical coherence photoacoustic microscopy: accomplishing optical coherence tomography and photoacoustic microscopy with a single light source," Journal of Biomedical Optics, Mar. 2012, pp. 030502-1-030502-3, vol. 17, No. 3.

Liu et al., "Optical coherence photoacoustic microscopy for in vivo multimodal retinal imaging," Optics Letters, Apr. 2015, pp. 1370-1373, vol. 40, No. 7.

Boettner et al., "Transmission of the ocular media," Investigative Ophthalmology and Visual Science, Dec. 1962, pp. 776-783, vol. 1, No. 6.

Weiter et al., "Retinal pigment epithelial lipofuscin and melanin and choroidal melanin in human eyes," Investigative Ophthalmology and Visual Science, Feb. 1986, pp. 145-152, vol. 27, No. 2.

Venecia et al., "Clinicopathologic correlations in diabetic retinopathy I. Histology and fluorescein angiography of microaneurysms," Archives of Ophthalmology, Oct. 1976, pp. 1766-1773, vol. 94.

Singh et al., "Fourier domain optical coherence tomographic and auto-fluorescence findings in indeterminate choroidal melanocytic lesions," British Journal of Ophthalmology, Oct. 2009, pp. 474-478, vol. 94.

Holz et al., "Simultaneous confocal scanning laser fluorescein and indocyanine green angiography," American Journal of Ophthalmology, Feb. 1998, pp. 227-236, vol. 125, No. 2.

Sparrow et al., "RPE lipofuscin and its role in retinal pathobiology," Experimental Eye Research, May 2005, pp. 595-606, vol. 80.

Delori et al., "Vitreous fluorophotometry in diabetics: study of artifactual contributions," Graefe's Archive for Clinical and Experimental Ophthalmology, Feb. 1985, pp. 215-218, vol. 222.

Povazay et al., "Visible light optical coherence tomography," International Symposium on Biomedical Optics, Jun. 2002, pp. 90-94, vol. 4619.

Pokorny et al., "Aging of the human lens," Applied Optics, Apr. 1987, pp. 1437-1440, vol. 26, No. 8.

* cited by examiner

QUANTITATIVE RETINAL AUTOFLUORESCENCE MAPPING WITH MULTIMODAL IMAGING TECHNOLOGY

GOVERNMENT SUPPORT

This invention was made with government support under Grant/Contract Number R01 EY019951 awarded by the National Institute of Health. The government has certain rights in the invention.

BACKGROUND

Lipofuscin is a complex lipid/protein aggregate formed in the retinal pigment epithelium (RPE) of the eye as nondegradable end products from phagocytosis of shed photoreceptor outer segments [7]. Lipofuscin granules are considered to be toxic to the RPE and thought to contribute to the pathogenesis of age-related macular degeneration (AMD) [8,9]. Rapid accumulation of lipofuscin and maculopathy can lead to conditions such as Stargardt disease, in which a lack of functional ABCA4 is evident (ATP-Binding Cassette, subfamily A, member 4).

Instruments such as optical coherence tomography (OCT) [1,2] and retinal auto-fluorescence (AF) imaging [3,4] are important imaging modalities in both ophthalmic clinics and research, each capable of imaging different aspects of the retina. OCT is a low-coherence interferometry based imaging modality and primarily provides structural imaging of the retina with microscopic depth resolution. Because lipofuscin is the major source of AF, it can be assessed by monitoring retinal AF. Retinal AF imaging maps the distribution of lipofuscin in the RPE.

AF signals emitted by lipofuscin travel through different retinal layers and the anterior segments of the eye before reaching an imaging receiver. The fluorescent signals will therefore be affected and attenuated by those layers, which can have different optical properties.

Existing retinal AF technologies do not take into consideration the attenuation of fluorescent signals by the media present in their optical path. Thus, the AF images by existing technologies do not accurately reflect the true level of AF in the RPE. Additionally, because the optical properties of the media in the optical path may differ among different individuals, as well as at different ages and pathological conditions in the same individual, it is difficult to compare images from different individuals and in the same individual at different times by using existing AF imaging technologies.

BRIEF SUMMARY

Embodiments of the subject invention provide imaging systems and methods of using the same for monitoring the quantity of fluorescent pigment (e.g., lipofuscin) in the retinal pigment epithelium (RPE) layer of the retina in vivo, relying on a combination of imaging modalities. In light of the limitations of related art methods discussed above, there remains a need in the art for imaging technologies that are capable of monitoring levels of lipofuscin levels for retinal disease tracking and treatment; embodiments of the subject invention can meet this need.

In some embodiments, various imaging modalities provided herein can be integrated into a single system and can be excited by a single broadband light source. Technologies provided herein can correct the influence of varying optical properties found in the optical path between the RPE layer and an image receiver.

Advantageously, embodiments of the subject invention can help establish standard lipofuscin auto-fluorescence (AF) levels for different age groups, delineate correlation between abnormal AF intensities and diseases stages both locally (i.e., for one individual) and globally (i.e., for a population), and to measure changes in AF as an outcome measurement of a given treatment, such as a clinical trial. Further, because existing retinal imaging technologies have been widely applied in ophthalmology clinics, systems and methods provided herein can readily replace the existing technologies for effective monitoring of lipofuscin in various applications.

BRIEF DESCRIPTION OF DRAWINGS

In FIG. 1, the following abbreviations are used—SC: supercontinuum; SLD: superluminescent diode; DM1-2: dichroic mirror; L1-3: Achromatic lens; LPF: long-pass filter; PH: pinhole; FP1-7: Fiber collimating port; ISO: Isolator; FC1-2: 3 dB fiber coupler; PC1-2: Polarization controller; G1-2: BK-7 glass plate; M1-2: Mirror; and IRIS1-2: Iris.

DETAILED DESCRIPTION

Embodiments of the subject invention provide novel and advantageous imaging systems and methods of using the same for monitoring the quantity of fluorescent pigment (e.g., lipofuscin) in the retinal pigment epithelium (RPE) layer of a retina in vivo, relying on a combination of imaging modalities.

In some embodiments, a method of imaging the retina of a subject can use an integrated imaging system that comprises a spectral-domain optical coherence tomography (SD-OCT) system and an auto-fluorescence (AF) system.

The complementary nature of the contrast mechanisms of SD-OCT and AF allows theses imaging modalities to be integrated into a single system and advantageously be excited by a single light source. The integrated imaging system can be illuminated using one or more light sources built into the SD-OCT system. For example, the OCT system can comprise at least one subsystem, each subsystem capable of illuminating incident light having a distinct center wavelength (each subsystem can be capable of illuminating incident light of different wavelengths from that of the other subsystems, or one or more of the subsystems can be capable of illuminating incident light of the same wavelength as at least one other subsystem).

In some embodiments, the OCT system can comprise a near-infrared (NIR) light source and a visible (VIS) light source. The NIR light source enables OCT images to be captured by illuminating an incident light having a center wavelength in a range of from 700 nm to 3000 nm (or about 700 nm to about 3000 nm), for example in a range of 800 nm to 1000 nm. In an embodiment, the wavelength of the NIR light source is centered in a range of from 800 nm to 900 nm. All ranges provided herein are inclusive of the endpoints.

Because images of retinal AF are acquired with broadband visible light as a source of fluorophore excitation, the OCT system can comprise a VIS light source to enable multimodal imaging (i.e., OCT and AF) in the integrated system. In some embodiments, the VIS incident light can have a center wavelength in a range of from 380 nm to 750 nm (or about 380 nm to about 750 nm), or in a range of from 400 nm to 600 nm. In an embodiment, the wavelength required for retinal AF excitation is in a range of from 470 nm to 490 nm.

Quantification of AF intensity arising from lipofuscin is important for tracking the pathogenesis of eye diseases such as age-related macular degeneration (AMD) and Stargardt disease within an individual and between different individuals of the same age group, for example. However, it is difficult to accurately assess the true intensities of AF at the RPE because, during AF imaging, the incident light must travel through various tissues in the eye (i.e., the media) anterior to the RPE before exciting the fluorophores in the lipofuscin, and the AF signals generated in the RPE must travel through the same path before being detected by the imaging system. AF signals are thereby attenuated and affected by tissues anterior to RPE, including the cornea, the aqueous humor, the vitreous, and the lens, which have different optical properties. The signal attenuation by the media anterior to RPE is different among individuals and even in the same individual over time. Thus, incapability to assess true AF intensities makes it difficult to compare the accumulation of lipofuscin in one individual at different time points and between different individuals.

Embodiments of the imaging methods provided herein rely on depth information provided by the OCT modality within the integrated system to correct for the influence of media so that the calculation of the true AF intensity arising from the RPE can be obtained accurately. This can be achieved by simultaneously acquiring VIS-OCT images and/or AF images using the same incident light source. Because the OCT and AF imaging signals are generated by the same group of photons simultaneously, the images arising from different modalities are intrinsically registered and their signal intensities correlated. Though both the OCT and AF signals are affected by the optical properties of the retinal layers and other tissues in the anterior section of the eye, OCT images can be segmented to obtain the refection from the RPE layer, which can then be used to normalize the AF intensities to correct for the attenuation factors aforementioned.

Embodiments of the subject invention provide a model that describes the light intensity reflected from the retina attributed to three sources, or three distinct layers of the eye. The first layer is the media anterior to the RPE. The second layer is the RPE layer, where reflection by the RPE and absorption by the lipofuscin granules occurs. The third is the post-RPE layer, which includes the choroid and sclera. The intensity of the reflected light from the pre-RPE layer and the RPE layer can be expressed as:

$$I_{pre} = I_0 \cdot \tau_{pre}(\lambda)^2 \cdot R_{pre}(\lambda) \quad (1)$$

$$I_{RPE} = I_0 \tau_{pre}(\lambda)^2 \cdot [1 - R_{pre}(\lambda)]^2 \cdot \tau_{RPE}(\lambda)^2 \cdot R_{RPE}(\lambda) \quad (2)$$

where $I_0$ is the light intensity incident into the eye, $I_{pre}$ and $I_{RPE}$ are the light intensities reflected from the pre-RPE and RPE layer, respectively, $\tau_{pre}$ and $\tau_{RPE}$ are the transmittance of the pre-RPE and RPE layer, respectively, and $R_{pre}$ and $R_{RPE}$ are the reflectance of the pre-RPE and RPE layer, respectively.

The lipofuscin fluorescence intensity ($I_{AF\text{-}RPE}$) detected can be expressed as:

$$I_{AF\text{-}RPE} = I_0 \tau_{pre}(\lambda)^2 \cdot [1 - R_{pre}(\lambda)]^2 \cdot \varepsilon \cdot C \cdot d \cdot Q \cdot A_d \quad (3)$$

where $\varepsilon$ is the extinction coefficient of the fluorescent pigment (i.e., lipofuscin), C is the concentration of lipofuscin, d is the thickness of the RPE layer, Q is the quantum yields of the fluorescence, and $A_d$ is the detecting efficiency of the integrated imaging system that can be attributed to factors including the detection solid angle, the response of the photomultiplier tube employed in the AF imaging system, the gain of the circuitry, and the digitization coefficient.

Assuming that $\tau_{pre}$ and $R_{pre}$ are the same for excitation light and the fluorescent, the ratio of the AF and OCT signals can be expressed by:

$$\frac{I_{AF}}{I_{RPE}} = \frac{\varepsilon \cdot C \cdot d \cdot Q \cdot Ad}{\tau_{RPE}^2(\lambda) \cdot R_{RPE}(\lambda)} \quad (4)$$

This assumption is made based on reasonable analysis. In the anterior segments of the retina, light attenuation in the visible spectrum is mainly determined by the scattering coefficients of the retinal tissues and light absorption can be ignored. Thus, $\tau_{pre}$ is close to unity for the anterior segments. Light transmission is mainly determined by $(1-R_{pre})$, which slightly increases with wavelength in the visible spectrum [33]. For the retinal tissues anterior to the RPE, light absorption is mainly caused by hemoglobin in the retinal blood vessels, whose overall absorption coefficient increases with wavelength in the spectral range from about 480 nm to about 570 nm. Meanwhile, in the same spectral range light scattering decreases with wavelength. As a result, the overall effect of the ocular tissues anterior to the RPE layer ($1-R_{pre}$). $\tau_{pre}$ may remain relatively constant for the excitation and AF light.

In many embodiments, all the parameters in Equation (4) related to the incident light intensity and the transmission of various eye components anterior to the RPE layer can be eliminated, leading to an absolute measure of the AF intensity arising from pigments in the RPE.

In some embodiments, $\tau_{pre}$ and $R_{pre}$ are functions of the concentrations of both melanin and lipofuscin in the RPE layer. Lipofuscin and melanin both exist in the RPE cells as fluorescent granules. Their relative concentrations can affect the values of $\tau_{pre}$ and $R_{pre}$. While lipofuscin accumulates during aging, melanin will likely decrease [34]. The decrease in melanin would contribute inversely to $\tau_{pre}$ and $R_{pre}$. For example, the increase of lipofuscin can reduce $\tau_{pre}$ but increase $R_{pre}$.

In some embodiments, the normalized AF intensity can be determined simply by using the known instrument settings of the integrated imaging system, which can be calibrated with a standard imaging target or a phantom system.

In some embodiments, in addition to removing the effects of optical attenuation in the AF signals, the normalization method provided herein can also remove effects of factors such as optical misalignment, thus retaining only the factors describing the optical properties of the RPE.

Because each imaging modality of the integrated system has been widely implemented in ophthalmology clinics, the integrated system provided herein can be readily applied in in-vivo settings for monitoring lipofuscin levels in individuals. Advantageously, embodiments of the subject invention can obtain quantitative AF intensities accurately; thus, they can help establish standard lipofuscin AF levels for different age groups, delineate correlation between abnormal AF intensities and diseases stages both locally and globally, and to measure changes in AF as an outcome measurement of a given treatment, such as a clinical trial. Furthermore, because existing retinal imaging technologies have been widely applied in ophthalmology clinics, systems and methods provided herein can readily replace the existing technologies for effective monitoring of lipofuscin in various applications.

The following are examples that illustrate the aforementioned embodiments and should not be construed as limiting. All of the chemical supplies provided herein, unless otherwise noted, were obtained via commercial sources and are readily available for procurement.

EXAMPLES

Example 1—Structure of the Integrated Imaging System

Figure 1:
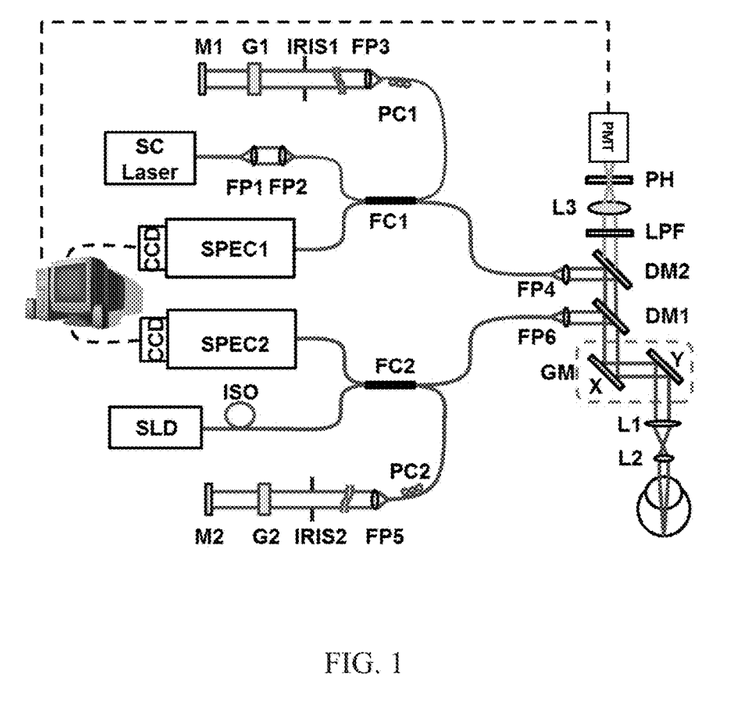
FIG. 1 is a schematic of an integrated imaging system according to an embodiment of the subject invention.

A schematic of an embodiment of the imaging system is shown in FIG. 1. Referring to FIG. 1, the system has two SD-OCT subsystems: one operates in the NIR region (FIG. 1; red lines) and the other in the VIS region (FIG. 1; blue lines). The VIS-OCT uses a supercontinuum laser (SC) source (EXB-6, SuperK EXTREME, NKT Photonics, Denmark) equipped with a variable band-pass filter (SuperK Varia, NKT Photonics). The filtered output light (center wavelength: 480 nm, bandwidth: 20 nm, 80 MHz pulse rate) is delivered though a fiber delivery module. The VIS light is coupled into the source arm of a single-mode optical fiber-based Michelson interferometer. The NIR-OCT uses a superluminescent diode (SLD-37-HP, center wavelength: 840 nm, bandwidth: 50 nm, Superlum, Russia).

After passing through an optical fiber isolator, the NIR light is coupled into another single-mode fiber-based Michaelson interferometer. The visible and NIR light beams, after exiting their corresponding optical fibers in the sample arms, are collimated and combined by using two dichroic mirrors (DM1: NT43-955, Edmund Optics and DM2: DMLP505, Thorlabs). The combined light beam is scanned by a x-y galvanometer (6215H, Cambridge) scanner, and delivered into the eye by the combination of a relay lens (L1, f=75 mm, achromatic) and an ocular lens (L2, f=20 mm, achromatic). The VIS light power was 500 µW before entering the eye, while the NIR light at the same location was 600 µW.

In the detection arm of each OCT subsystem, the reflected light from the sample and reference arms is collimated and detected by a spectrometer (SPEC1-2). The VIS-OCT spectrometer has an 1800 lines/mm transmission grating, a multi-element imaging lens (f=150 mm), and a line scan charge-coupled device (CCD) camera (Aviiva-SM2-CL-2010, 2048 pixels with 10 µm pixel size operating in 12-bit mode, e2V). The NIR-OCT uses a spectrometer with the same parameters as described in our previous publications [17].

The system for AF detection is similar to that described in previous studies [13]. In short, the back-traveling fluorescent photons emitted from the fluorophore pass through the two dichroic mirrors and a long-pass filter (FGL515M, cut-on wavelength: 515 nm, Thorlabs), and are then focused into a 25 µm pinhole by an achromatic doublet with a focal length of 30 mm (L3).

The AF photons are detected by a photomultiplier tube (PMT) module (PMM02, Thorlabs). The outputs of the PMT are digitized by a multifunction data acquisition board (DAQ, PCIe-6361, National Instruments) at a sampling rate of 2 M/s. At each scanning position on the retina, a total of 80 points corresponding to a sampling length of 30 µs were acquired. The amplitudes of the AF signal of these 80 points were averaged to form a single pixel of the AF image. Synchronization of the AF data acquisition, scanning of the galvanometer scanner and the OCT image acquisition was controlled by a multifunction DAQ board.

Example 2—Construction and Testing of a Phantom System

Figures 2A, 2B:
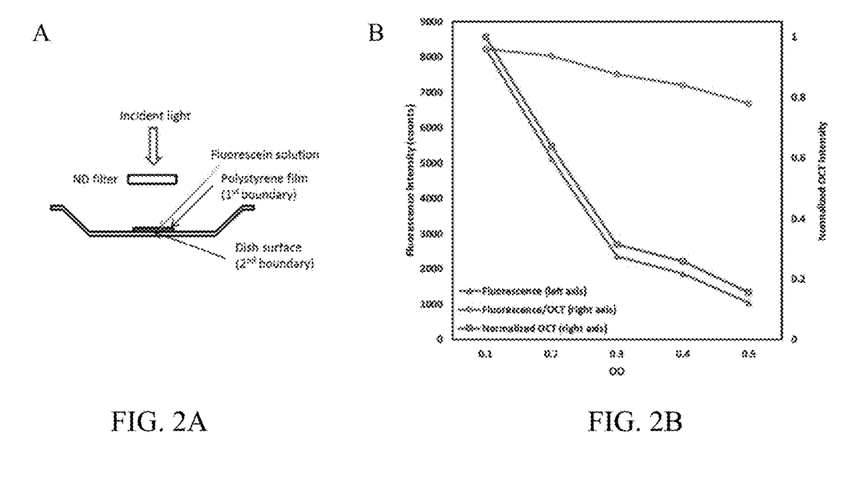
FIG. 2A is a schematic of a phantom system according to an embodiment of the subject invention.
FIG. 2B is a plot of fluorescence intensity (counts; left-side y-axis) and normalized optical coherence tomography (OCT) intensity (right-side y-axis) versus OD, showing that the auto-fluorescence (AF)/OCT signals (the AF intensity divided by the 2nd boundary OCT intensity; green line that is the highest on the right side of the plot and has the circular data points) were not influenced by the OD values of the ND filter, unlike the raw AF signals (blue line that is the lowest at the right side of the plot and has the triangular data points)) and OCT signals (red line that is second-lowest at the right side of the plot and has the square data points). The linear decrease of AF/OCT was due to accumulated bleaching of the dye.

To further test the imaging system and the theoretical models, a phantom was built to simulate light attenuation by tissues anterior to the RPE (FIG. 2A). The phantom comprises three components: a plastic weighing dish as the container, fluorescein sodium solution in the container to simulate lipofuscin, and a transparent polystyrene membrane to cover the fluorescent dye solution and control the thickness of the sample. A set of ND filters (nominal OD values of 0.1-0.5) was placed in front of the phantom for light attenuation.

The phantom setup has two boundaries in the OCT cross-sectional image: the first is the polystyrene membrane and the second is the surface of the weighing dish. OCT and fluorescent images were simultaneously acquired. The OD value of the sample was measured to be 1.26±0.02. By segmentation the intensity of the OCT reflection was obtained from the second boundary (FIG. 2; red curve). As the OD value increased, both the fluorescent (FIG. 2B; blue curve) and OCT signals decreased. But the normalized fluorescent signals (FIG. 2B; green curve) calculated using Eq. (4) showed only a gradual and linear decrease, which was caused by accumulated bleaching of the dye as the measurements were taken sequentially from low to high OD values. Each measurement caused partial bleaching of the dye and the effect accumulated unless the time interval among measurements was sufficient for the dye to recover.

It is clear that the normalized AF signals are independent of the OD values of the ND filter. As seen in FIG. 2B, the use of an OD=0.3 filter resulted in a large deviation from the nominal OD value, which made the measured AF and OCT signal curves "non-linear" (FIG. 2B; red and blue curves), and yet the linearity of the normalized AF curve was not affected (FIG. 2B; green curves). Results of these experiments demonstrate that OCT signals can be used as an internal reference to minimize the effects of media anterior to the RPE as expected.

It is important to note that in the phantom study, higher dye concentration would reduce the signal intensity from the second boundary. When the concentration of the dye is higher than a certain level, determined by the sensitivity of the OCT, the second boundary of the phantom could no longer be reliably imaged. In such an extreme and unlikely situation, the normalization method cannot be used.

Example 3—In-Vivo Simultaneous VIS-OCT and Retinal AF

To test the capabilities of the imaging technique, the retinas of albino Sprague Dawley rats (SD rats, Taconic) were imaged. All the experiments were performed in compliance with the ARVO Statement for the Use of Animals in Ophthalmic and Vision Research and with the guidelines of the Florida International University's Institutional Animal Care and Use Committee.

The animals were anesthetized by intraperitoneal injection of a cocktail containing ketamine (54 mg/kg body weight) and xylazine (6 mg/kg body weight). The pupil was dilated with 10% phenylephrine solution. Drops of artificial tear were applied during the imaging to prevent cornea dehydration and cataract formation. The rat was restrained in an animal mount, which was placed in a five-axis platform.

Figure 3A:
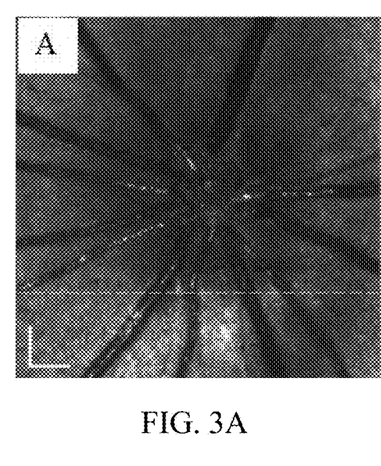
FIG. 3A-3C show a visible-OCT (VIS-OCT) fundus image (FIG. 3A), an AF image (FIG. 3B), and a VIS-OCT B-scan image (FIG. 3C) simultaneously acquired from a rat retina in vivo. The scale bar is 200 μm.
Figure 3B:
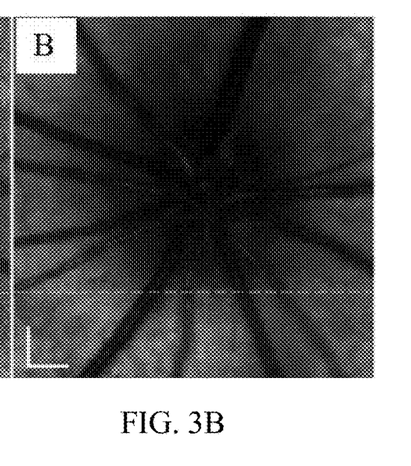
Figure 3C:
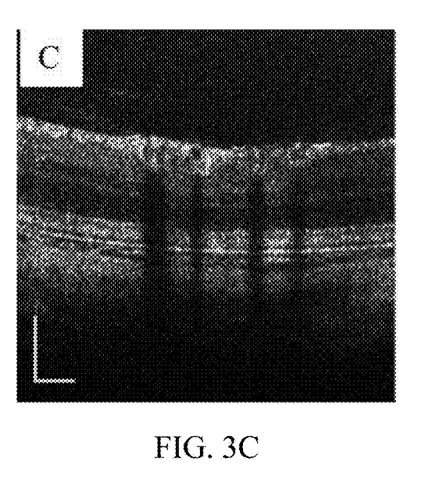

FIGS. 3A-3C demonstrate examples of the simultaneously acquired VIS-OCT (FIGS. 3A and 3C) and AF (FIG. 3B) images of the retina of an SD rat (age: 12 months; body weight: 500 g). FIG. 3A is the projected OCT fundus image generated from the acquired 3D VIS-OCT dataset [20]. FIG. 3C is the VIS-OCT cross-sectional B-scan image, the location of which is marked as a dotted line in FIGS. 3A and 3B, respectively. The OCT dataset consists of 512 (horizontal)× 128 (vertical) A-scans. Since the OCT and AF images were generated from the same photons, it can be seen that FIGS. 3A and 3B are precisely registered.

Figure 4A:
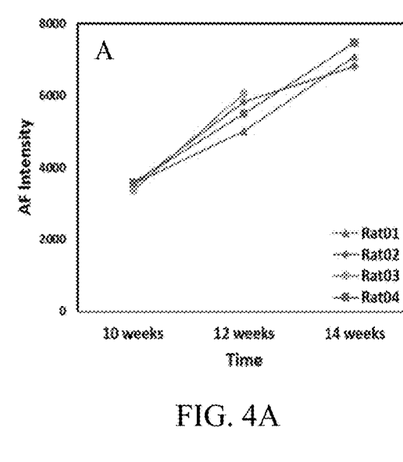
FIGS. 4A-4B show the original AF intensities (FIG. 4A) and the normalized AF intensities (FIG. 4B) of four rats being followed for a period of four weeks. Normalization was performed using the retinal pigment epithelium (RPE) image intensities calculated from the segmented OCT images.

In previous studies [13], four SD rats (10-week-old) were imaged every two weeks (one rat died after the second imaging) to monitor their AF in the retinas for 4 weeks. The imaging conditions, including the focusing and the power of the probe light, the position of the reference arm, and the depth of the retina in the OCT image, were kept the same in each imaging experiment. The mean AF intensity counts over the entire imaged area of the 4 rats at different time points are shown in FIG. 4A. The accumulation of lipofuscin in the RPE cells was evidenced by the increased AF image intensities over time.

Figure 4B:
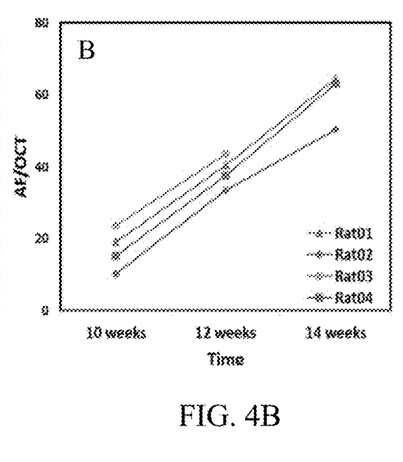

The mean AF intensity counts were then normalized with the RPE's OCT signal intensities obtained by manually segmenting the RPE layer and averaged over the entire imaged area. The normalized AF intensity was calculated by using Eq. (4). From the raw mean AF intensity counts, significant increases can be seen over the 4-week period, but the rate of increase in each animal differed significantly. When the normalized data were used (FIG. 4B), the rates of increase among animals were quite similar. Note that the levels of $I_{AF}$ in FIG. 4B between animals are not normalized to a common reference, and thus they cannot be compared quantitatively if not all the imaging conditions including the eye conditions are known. The Y axis scale in FIG. 4B has no specific physical meaning in this case.

All rats in the experiment were of the same age and housed under the same lighting conditions. It is reasonable to believe that the rate of lipofuscin accumulation is similar for all the rats. Before normalization using Eq. (4) the rate of AF intensity increased (i.e., the rate of lipofuscin accumulation increased) and was significantly different among the different rats. After normalization using Eq. (4), the AF intensities of different rats increased over time at similar rate. Further, as mentioned earlier, prior art study shows a linear correlation between aging and lipofuscin accumulation [21] which can be better observed when using Eq. (4) for normalization.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. D. Huang, E. A. Swanson, C. P. Lin, J. S. Schuman, W. G. Stinson, W. Chang, M. R. Hee, T. Flotte, K. Gregory, and C. A. Puliafito, "Optical coherence tomography," Science 254, 1178-1181 (1991).
2. M. Wojtkowski, V. J. Srinivasan, T. H. Ko, J. G. Fujimoto, A. Kowalczyk and J. S. Duker, "Ultrahigh-resolution, high-speed, Fourier domain optical coherence tomography and methods for dispersion compensation," Optics Express 12(11) 2404-22 (2004).
3. A. D. Singh, R. N. Belfort, K. Sayanagi, and P. K. Kaiser, "Fourier domain optical coherence tomographic and autofluorescence findings in indeterminate choroidal melanocytic lesions," British Journal of Ophthalmology 94, 474-478 (2010).
4. F. C. Delori, C. K. Dorey, G. Staurenghi, O. Arend, D. G. Goger, and J. J. Weiter, "In vivo fluorescence of the ocular fundus exhibits retinal pigment epithelium lipofuscin characteristics," Investigative ophthalmology & visual science 36(3), 718-29 (1995).
5. G. de Venecia, M. Davis, and R. Engerman, "Clinicopathologic Correlations in Diabetic Retinopathy I. Histology and Fluorescein Angiography of Microaneurysms," Arch. Ophthalmol 94(10), 1766-1773 (1976).
6. F. G. Holz, C. Bellmann, K. Rohrschneider, R. O. W. Burk, and H. E. Voölcker, "Simultaneous confocal scanning laser fluorescein and indocyanine green angiography," American J. of Ophthalmology 125(2), 227-236 (1998).
7. Boulton M, McKechnie N M, Breda J, Bayly M, Marshall J. "The formation of autofluorescent granules in cultured human RPE," Investigative ophthalmology & visual science 30(1), 82-9 (1989).
8. J. R. Sparrow, M. Boulton, "RPE lipofuscin and its role in retinal pathobiology," Experimental eye research 80(5), 595-606 (2005).
9. E. J. Johnson, "Age-related macular degeneration and antioxidant vitamins: recent findings," Current opinion in clinical nutrition and metabolic care 13(1), 28-33 (2010).
10. B. Povazay, A. A. Apolonski, A. Unterhuber, B. Hermann, K. K. Bizheva, H. Sattmann, P. S. J. Russell, F. Krausz, A. F. Fercher, and W. Drexler, "Visible light optical coherence tomography," Proc. SPIE 4619, 90-94 (2002).
11. X. Zhang, J. Hu, R. W. Knighton, X.-R. Huang, C. A. Puliafito, and S. Jiao, "Dual-band spectral-domain optical coherence tomography for in vivo imaging the spectral contrasts of the retinal nerve fiber layer," Optics Express 19, 19653-19659 (2011).
12. C. Dai, X. Liu, and S. Jiao, "Simultaneous optical coherence tomography and autofluorescence microscopy 13. M. S. Jiang, T. Liu, X. J. Liu, S. L. Jiao, "Simultaneous optical coherence tomography and lipofuscin autofluorescence imaging of the retina with a single broadband light source at 480 nm," Biomed Opt Express 5(12), 4242-4248 (2014).
14. J. Yi, Q. Wei, W. Liu, V. Backman, H. F. Zhang, "Visible-light optical coherence tomography for retinal oximetry," Optics letters 38(11), 1796-1798 (2013).
15. F. Delori, J. P. Greenberg, R. L. Woods, J. Fischer, T. Duncker, J. Sparrow, R. T. Smith, "Quantitative measurements of autofluorescence with the scanning laser ophthalmoscope," Investigative ophthalmology & visual science 52(13), 9379-90 (2011).
16. J. Pokorny, V. C. Smith, M. Lutze, "Aging of the human lens," Applied optics 26(8), 1437-40 (1987).
17. C. Dai, X. Liu, H. F. Zhang, C. A. Puliafito, and S. Jiao, "Absolute retinal blood flow measurement with a dual-beam Doppler optical coherence tomography," Investigative Ophthalmology & Visual Science 54, 7998-8003 (2013).
18. J. van de Kraats, T. T. Berendschot, D. van Norren, "The pathways of light measured in fundus reflectometry," Vision research 36(15), 2229-47 (1996).
19. J. I. W. Morgan, E. N. Pugh, "Scanning Laser Ophthalmoscope Measurement of Local Fundus Reflectance and Autofluorescence Changes Arising from Rhodopsin Bleaching and Regeneration," Investigative Ophthalmology & Visual Science 54(3) 2048-59 (2013).
20. S. Jiao, R. Knighton, X. Huang, G. Gregori, and C. Puliafito, "Simultaneous acquisition of sectional and fundus ophthalmic images with spectral-domain optical coherence tomography," Optics Express 13, 444-452 (2005).
21. F. C. Delori, G. Staurenghi, O. Arend, C. K. Dorey, D. G. Goger and J. J. Weiter, "In vivo measurement of lipofuscin in Stargardt's disease—Fundus flavimaculatus," Investigative ophthalmology & visual science 36(11) 2327-31 (1995).
22. F. C. Delori, S. E. Bursell, A. Yoshida and J. W. McMeel, "Vitreous fluorophotometry in diabetics: study of artifactual contributions," Graefes Arch Clin Exp Ophthalmol 222(4-5), 215-8 (1985).
23. J. R. Sparrow, N. Fishkin, J. Zhou, B. Cai, Y. P. Jang, S. Krane, Y. Itagaki and K. Nakanishi, "A2E, a byproduct of the visual cycle," Vision research 43(28) 2983-90 (2003).
24. J. R. Sparrow, E. Gregory-Roberts, K. Yamamoto, A. Blonska, S. K. Ghosh, K. Ueda and J. Zhou, "The bisretinoids of retinal pigment epithelium," Progress in retinal and eye research 31(2), 121-35 (2012).
25. J. R. Sparrow and M. Boulton, "RPE lipofuscin and its role in retinal pathobiology," Experimental eye research 80(5), 595-606 (2005).
26. O. Strauss, "The retinal pigment epithelium in visual function," Physiological reviews 85(3), 845-81 (2005).
27. P. D. Kiser, M. Golczak, K. Palczewski, "Chemistry of the retinoid (visual) cycle," Chem Rev. 114(1), 194-232 (2014).
28. B. M. Kevany and K. Palczewski, "Phagocytosis of retinal rod and cone photoreceptors," Physiology (Bethesda) 25(1), 8-15 (2010).
29. X. Zhang, H. F. Zhang, C. A. Puliafito, and S. Jiao, "Simultaneous in vivo imaging of melanin and lipofuscin in the retina with multimodal photoacoustic ophthalmoscopy," J. Biomed. Opt. 16, 080504 (2011).
30. X. Zhang, M. Jiang, A. A. Fawzi, X. A. Li, K. K. Shung, C. A. Puliafito, H. F. Zhang, and S. Jiao, "Simultaneous dual molecular contrasts provided by the absorbed photons in photoacoustic microscopy," Optics Letters 35, 4018-4020 (2010).
31. X. Zhang, H. F. Zhang, C. A. Puliafito, and S. Jiao, "Optical Coherence Photoacoustic Microscopy: accomplishing optical coherence tomography and photoacoustic microscopy with a single light source," J. Biomed. Opt. 17, 030502 (2012).
32. X. Liu, T. Liu, R. Wen, Y. Li, C. A. Puliafito, H. F. Zhang, and S. Jiao, "Optical coherence photoacoustic microscopy for in vivo multimodal retinal imaging," Opt. Letters 40, 1370-1373 (2015).
33. E. A. Boettner and J. R. Wolter, "Transmission of the ocular media," Invest.Ophthalmol.Vis.Sci. 1(6), 776-783 (1962).
34. J. Weiter, F. Delori, G. Wing and K. Fitch, "Retinal pigment epithelial lipofuscin and melanin and choroidal melanin in human eyes." Invest.Ophthalmol.Vis.Sci. 27(2), 145-152 (1986).

What is claimed is:

1. A method of imaging a retina in vivo, the method comprising:
   providing the retina to be imaged;
   providing a spectral-domain optical coherence tomography (SD-OCT) imaging system comprising a first subsystem having a near-infrared (NIR) light source and a second subsystem having a visible light (VIS) source;
   providing an auto-fluorescence (AF) imaging system, the AF imaging system being integrated with the SD-OCT subsystems such that the AF imaging system is illuminated by the light sources provided by the SD-OCT subsystems;
   acquiring SD-OCT images from the SD-OCT imaging system and AF images from the AF imaging system simultaneously, based on a light intensity reflected from the retina attributed to three layers of an eye including the retina,
   the SD-OCT imaging system further comprising an optical fiber isolator connected to the NIR light source.

2. The method according to claim 1, the NIR light source having a center wavelength in a range of from 700 nm to 3000 nm.

3. The method according to claim 1, the VIS light source having a center wavelength in a range of from 380 nm to 750 nm.

4. The method according to claim 3, the VIS light source being configured to induce the AF of one or more fluorescent pigments found in the retinal pigment epithelium (RPE) layer of the retina.

5. The method according to claim 4, the one or more fluorescent pigments comprising lipofuscin.

6. The method according to claim 1, further comprising:
   segmenting the SD-OCT images to obtain reflected light intensity in the retinal pigment epithelium (RPE) layer of the retina;
   normalizing the light intensity of the AF images using the segmented SD-OCT images to eliminate optical attenuation by the retina; and
   quantifying an absolute measure of light intensity arising from the AF of the RPE layer.

7. The method according to claim 6, the VIS light source having a center wavelength in a range of from 380 nm to 750 nm, and the VIS light source being configured to induce the AF of one or more fluorescent pigments found in the RPE layer of the retina.

8. A method of tracking the presence of a fluorescent pigment in the RPE of a subject, the method comprising:
performing the method according to claim 1 on the subject; and
correlating the absolute measure of light intensity arising from the AF of the RPE with the amount of the fluorescent pigment present in the RPE layer.

9. The method according to claim 8, the correlating of the absolute measure of light intensity arising from the AF of the RPE layer with the amount of the fluorescent pigment present in the RPE layer comprising the use of the following equation:

$$\frac{I_{AF}}{I_{RPE}} = \frac{\varepsilon \cdot C \cdot d \cdot Q \cdot Ad}{\tau_{RPE}^2(\lambda) \cdot R_{RPE}(\lambda)},$$

$I_{AF}$ being the light intensity arising from the AF of the RPE layer, $I_{RPE}$ being the light intensity arising from the RPE layer, $\tau_{RPE}$ being the transmittance of the RPE layer, $R_{RPE}$ being the reflectance of the RPE layer, $\varepsilon$ being the extinction coefficient of the pigment giving rise to the AF, C being the concentration of lipofuscin, d being the thickness of the RPE, Q being the quantum yields of the fluorescence, and $A_d$ being the detecting efficiency of the imaging systems.

10. The method according to claim 9, the fluorescent pigment being lipofuscin.

11. The method according to claim 1, further comprising:
segmenting the SD-OCT images to obtain reflected light intensity in the retinal pigment epithelium (RPE) layer of the retina.

12. An integrated imaging system for imaging a retina in vivo, the system comprising:
a spectral-domain optical coherence tomography (SD-OCT) imaging system comprising a first subsystem having a near-infrared (NIR) light source and a second subsystem having a visible light (VIS) source; and
an auto-fluorescence (AF) imaging system, the AF imaging system being integrated with the SD-OCT subsystems such that the AF imaging system is illuminated by the light sources provided by the SD-OCT subsystems,
the integrated imaging system being configured such that SD-OCT images are acquired from the SD-OCT imaging system and AF images are acquired from the AF imaging system simultaneously, based on a light intensity reflected from the retina attributed to three layers of an eye including the retina, and
the SD-OCT imaging system further comprising an optical fiber isolator connected to the NIR light source.

13. The system according to claim 12, the NIR light source having a center wavelength in a range of from 700 nm to 3000 nm, and
the VIS light source having a center wavelength in a range of from 380 nm to 750 nm.

14. The system according to claim 13, the VIS light source being configured to induce the AF of one or more fluorescent pigments found in the retinal pigment epithelium (RPE) layer of the retina.

15. The system according to claim 14, the one or more fluorescent pigments comprising lipofuscin.

16. The system according to claim 12, further comprising a fluorescein angiography (FA) imaging system integrated with the SD-OCT imaging system and the AF imaging system,
the integrated imaging system being configured such that SD-OCT images are acquired from the SD-OCT imaging system, AF images are acquired from the AF imaging system, and FA images are acquired from the FA imaging system simultaneously.

17. The system according to claim 16, the NIR light source having a center wavelength in a range of from 700 nm to 3000 nm, and
the VIS light source having a center wavelength in a range of from 380 nm to 750 nm.

18. The system according to claim 17, the VIS light source being configured to induce the AF of one or more fluorescent pigments found in the retinal pigment epithelium (RPE) layer of the retina, and
the one or more fluorescent pigments comprising lipofuscin.

19. A method of imaging a retina in vivo, the method comprising:
providing the retina to be imaged;
providing a spectral-domain optical coherence tomography (SD-OCT) imaging system comprising a first subsystem having a near-infrared (NIR) light source and a second subsystem having a visible light (VIS) source;
providing an auto-fluorescence (AF) imaging system, the AF imaging system being integrated with the SD-OCT subsystems such that the AF imaging system is illuminated by the light sources provided by the SD-OCT subsystems;
integrating a fluorescein angiography (FA) imaging system with the SD-OCT imaging system and the AF imaging system;
simultaneously acquiring SD-OCT images from the SD-OCT imaging system, AF images from the AF imaging system, and FA images from the FA imaging system, based on a light intensity reflected from the retina attributed to three layers of an eye including the retina;
segmenting the SD-OCT images to obtain reflected light intensity in the retinal pigment epithelium (RPE) layer of the retina;
normalizing the light intensity of the AF images using the segmented SD-OCT images to eliminate optical attenuation by the retina; and
quantifying an absolute measure of light intensity arising from the AF of the RPE layer,
the NIR light source having a center wavelength in a range of from 700 nm to 3000 nm,
the VIS light source having a center wavelength in a range of from 380 nm to 750 nm,
the VIS light source being configured to induce the AF of a fluorescent pigment found in the RPE layer of the retina,
the fluorescent pigment comprising lipofuscin, and
the SD-OCT imaging system further comprising an optical fiber isolator connected to the NIR light source.

20. A method of tracking the presence of a fluorescent pigment in the RPE of a subject, the method comprising:
performing the method according to claim 19 on the subject; and
correlating the absolute measure of light intensity arising from the AF of the RPE with the amount of the fluorescent pigment present in the RPE layer,
the correlating of the absolute measure of light intensity arising from the AF of the RPE layer with the amount of the fluorescent pigment present in the RPE layer comprising the use of the following equation:

$$\frac{I_{AF}}{I_{RPE}} = \frac{\varepsilon \cdot C \cdot d \cdot Q \cdot Ad}{\tau_{RPE}^2(\lambda) \cdot R_{RPE}(\lambda)}$$

$I_{AF}$ being the light intensity arising from the AF of the RPE layer, $I_{RPE}$ being the light intensity arising from the RPE layer, $\tau_{RPE}$ being the transmittance of the RPE layer, $R_{RPE}$ being the reflectance of the RPE layer, $\varepsilon$ being the extinction coefficient of the pigment giving rise to the AF, C being the concentration of lipofuscin, d being the thickness of the RPE, Q being the quantum yields of the fluorescence, and $A_d$ being the detecting efficiency of the imaging systems.

* * * * *